United States Patent
Albans et al.

(10) Patent No.: US 8,747,471 B2
(45) Date of Patent: Jun. 10, 2014

(54) VERTEBRAL IMPLANTS INCLUDING ASYMMETRIC ENDPLATE CONTOURS AND METHODS OF USE

(75) Inventors: William Albans, Southaven, MS (US); Eric S. Heinz, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1321 days.

(21) Appl. No.: 11/403,466

(22) Filed: Apr. 13, 2006

(65) Prior Publication Data

US 2007/0270958 A1    Nov. 22, 2007

(51) Int. Cl.
*A61F 2/44*    (2006.01)

(52) U.S. Cl.
USPC ...................................... 623/17.11

(58) Field of Classification Search
USPC ................. 606/61, 60, 246; 623/17.11–17.16
See application file for complete search history.

(56) References Cited

U.S. PATENT DOCUMENTS

| | | | |
|---|---|---|---|
| 6,350,283 B1 * | 2/2002 | Michelson | 623/17.11 |
| 6,997,955 B2 | 2/2006 | Zubok et al. | |
| 2002/0035400 A1 * | 3/2002 | Bryan et al. | 623/17.15 |
| 2003/0009224 A1 | 1/2003 | Kuras | |
| 2003/0100951 A1 * | 5/2003 | Serhan et al. | 623/17.16 |
| 2003/0120344 A1 | 6/2003 | Michelson | |
| 2004/0138753 A1 * | 7/2004 | Ferree | 623/17.11 |
| 2005/0096746 A1 | 5/2005 | Bryan et al. | |
| 2005/0149188 A1 * | 7/2005 | Cook et al. | 623/17.11 |
| 2005/0216086 A1 | 9/2005 | Marik et al. | |
| 2005/0216092 A1 | 9/2005 | Marik et al. | |
| 2005/0251261 A1 | 11/2005 | Peterman | |
| 2006/0217806 A1 * | 9/2006 | Peterman et al. | 623/17.11 |

OTHER PUBLICATIONS

Langrana, Noshir A., "Measurement and analyses of the effects of adjacent end plate curvatures on vertebral stresses." The Spine Journal, 2006, pp. 267-278, Issue 6, Elsevier Inc.
Pfirrmann, Christian W.A., et al., "Schmorl Nodes of the Thoracic and Lumbar Spine: Radiographic-Pathologic Study of Prevalence, Characterization, and Correlation with Degenerative Changes of 1,650 Spinal Levels in 100 Cadavers." Radiology, vol. 219, No. 2, May 2001, pp. 368-374.
Tan, Juay-Seng et al., "Interbody Device Shape and Size Are Important to Strengthen the Vertebra-Implant Interface." Spine, vol. 30, No. 6, 2005, pp. 638-644.

* cited by examiner

*Primary Examiner* — Anu Ramana
*Assistant Examiner* — Michael Araj

(57) ABSTRACT

An implant for insertion into a patient includes a superior surface disposed at a first end of the implant and an inferior surface disposed at a second, opposite end of the implant. The superior and inferior surfaces of the implant are constructed with curvatures that approximately match the morphology of vertebral endplates. The inferior surface and superior surface may include the same or different radii of curvature within the coronal and sagittal planes. The inferior surface and superior surface may be defined by spherical radii. The radius of the superior surface may be about 60 percent to 74 percent of the radius of the inferior surface.

24 Claims, 8 Drawing Sheets

VERTEBRAL IMPLANTS INCLUDING ASYMMETRIC ENDPLATE CONTOURS AND METHODS OF USE

BACKGROUND

Spinal implants are often used in the surgical treatment of spinal disorders such as degenerative disc disease, disc herniations, curvature abnormalities, and trauma. Many different types of treatments are used. In some cases, spinal fusion is indicated to inhibit relative motion between vertebral bodies. In other cases, dynamic implants are used to preserve motion between vertebral bodies. In yet other cases, relatively static implants that exhibit some degree of flexibility may be inserted between vertebral bodies.

Implants such as these may be positioned between vertebral bodies, with superior and inferior surfaces placed in contact with the vertebral bodies. Often, the bone-contact surfaces of these implants are configured with a surface texture, surface features, and natural or synthetic bone growth stimulators to promote osseointegration of the implant. The quality of the interface between a vertebral implant and a vertebral body may affect the integrity and strength of the bond that forms between the vertebral body and the implant. Ineffective fusion at the bone-contact surface may lead to subsidence of the vertebral implants over time, and often leads to spinal instability, angular deformities, and planar translations.

One conventional approach uses mechanical means to prepare the surface of a vertebral body prior to inserting the vertebral implant. For example, the vertebral body could be planed or otherwise prepared to mate with a corresponding surface of an implant. However, this process of preparing the bone for implant insertion thins the vertebral endplates and has the potential to compromise the strength of the vertebral body. The bone preparation step also adds time to the procedure and trauma to the patient. Therefore, certain conventional vertebral implants are not configured to take advantage of the natural anatomy of vertebral bodies so as to eliminate or reduce this bone preparation step.

SUMMARY

Illustrative embodiments disclosed herein are directed to a vertebral implant that includes a superior surface disposed at a first end of the implant and an inferior surface disposed at a second, opposite end of the implant. The superior and inferior surfaces may be disposed on a common body or on separate end plate members. The superior and inferior surfaces of the implant are constructed with curvatures that approximately match the morphology of vertebral endplates. The inferior surface and superior surface may include the same or different radii of curvature within the coronal and sagittal planes. The inferior surface and superior surface may be defined by spherical radii. In one embodiment, the inferior surface includes a first radius of curvature and the superior surface includes a second radius of curvature that may be about 60 percent to about 74 percent of the first radius of curvature. In one embodiment, the first radius of curvature may be within a range between about 80 mm and about 100 mm. In one embodiment, the second radius of curvature may be within a range between about 50 mm and about 70 mm.

DETAILED DESCRIPTION

Figure 1:
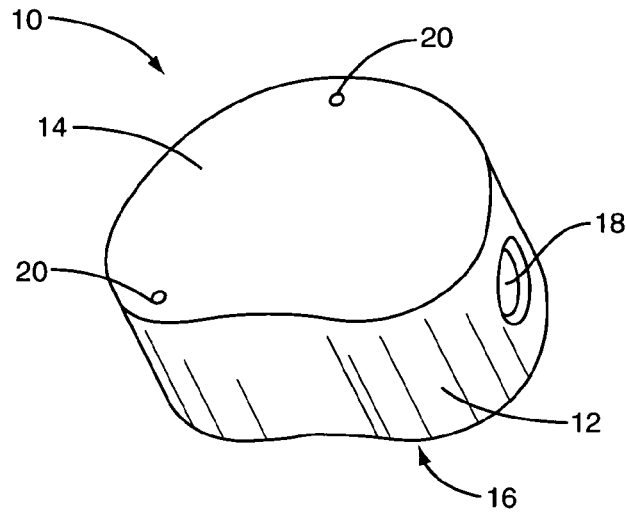
FIG. 1 is a perspective view of a vertebral implant according to one or more embodiments.

The various embodiments disclosed herein relate to a vertebral implant in which bone-contact surfaces are constructed with contours that approximately match the natural anatomy of vertebral bodies in the human spine. One example of an implant with anatomically-shaped bone-contact surfaces is identified generally by the number 10 in FIG. 1. The representative vertebral implant 10 is a disc replacement implant that is inserted between vertebral bodies of a patient as part of a disc replacement surgery. The exemplary vertebral implant 10 includes a perimeter wall 12 that extends between a superior surface 14 and an inferior surface 16. The superior surface 14 and inferior surface 16 are bone-contact surfaces in that they are positioned adjacent to and facing a vertebral endplate once the vertebral implant 10 is inserted into a patient.

The vertebral implant 10 shown in FIG. 1 includes a kidney shape, though other shapes may be used. In further embodiments, the vertebral implant 10 may take on other types of configurations, such as, for example, a circular shape, semi-oval shape, bean-shape, D-shape, elliptical-shape, egg-shape, or any other shape that would occur to one of skill in the art. The vertebral implant 10 may take on substantially solid configurations, such as, for example, block-like or plate-like configurations that do not define an open inner region. In other embodiments, the vertebral implant 10 could also be described as being annular, U-shaped, C-shaped, V-shaped, horseshoe-shaped, semi-circular shaped, semi-oval shaped, or other similar terms defining an implant including at least a partially open or hollow construction.

The vertebral implant 10 may be constructed from biocompatible metal alloys such as titanium, cobalt-chrome, and stainless steel. The vertebral implant 10 may be constructed from non-metallic materials, including for example, ceramics, resins, or polymers, such as UHMWPE and implantable grade polyetheretherketone (PEEK) or other similar materials (e.g., PAEK, PEKK, and PEK). The vertebral implant 10 may be constructed of synthetic or natural bone or bone composites. Those skilled in the art will comprehend a variety of other material choices that are suitable for the illustrated vertebral implant 10.

The exemplary vertebral implant 10 includes one or more apertures 18 disposed about the perimeter wall 12 that provide a location at which to grasp the vertebral implant 10 during surgical installation. In some instances, the vertebral implant 10 is constructed of a material that is solid, but somewhat flexible or compressible. Thus, the apertures 18 may contribute to the overall flexibility and/or compressibility of the vertebral implant 10.

Furthermore, certain materials that are used to construct the vertebral implant 10 may be radiolucent in that they are not visible in a radiograph. Accordingly, the vertebral implant may include a plurality of visualization markers 20 that improve the radiographic visibility of the vertebral implant 10 during and after installation of the vertebral implant 10. The markers 20 may be oriented so they pass from the superior surface 14 to the inferior surface 16 as shown. Further, the markers 20 may be disposed towards the perimeter wall 12 (as shown) or disposed away from the perimeter wall 12. The markers 20 may be disposed on or in the perimeter wall 12.

Figure 2:
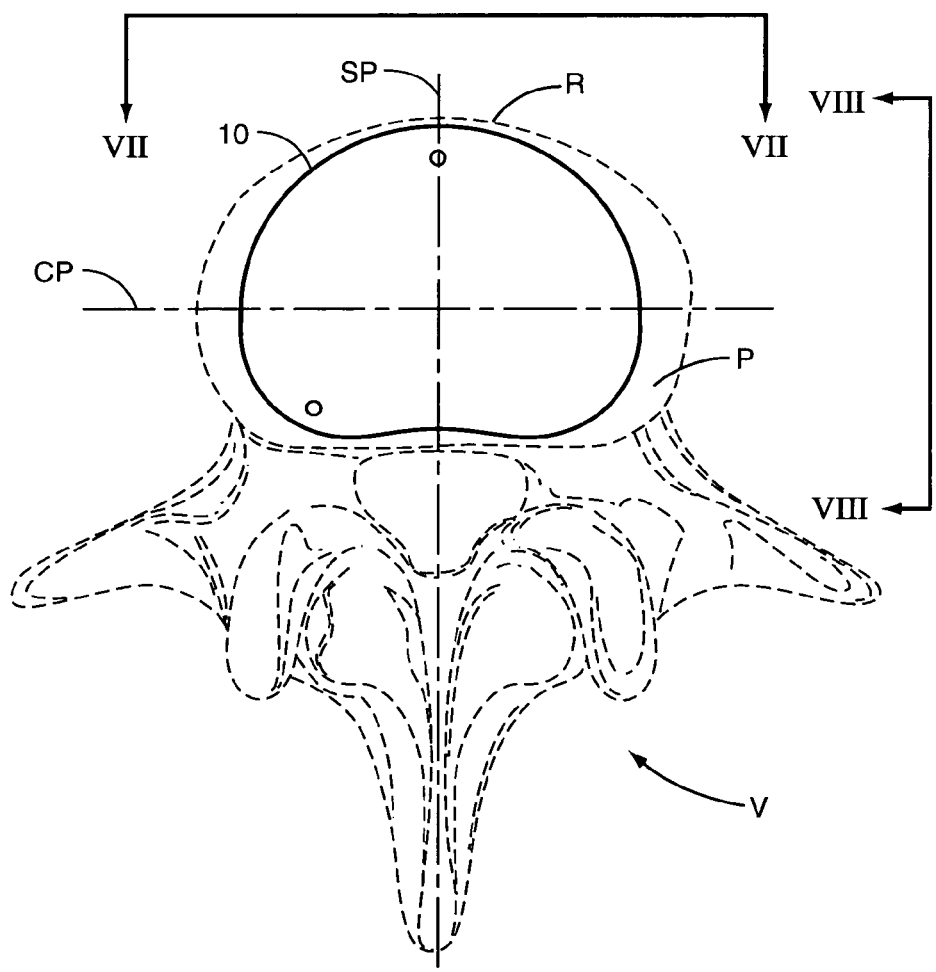
FIG. 2 is a top view of a vertebral implant according to one or more embodiments shown relative to a vertebral body.

FIG. 2 depicts a top view of the exemplary vertebral implant 10 oriented relative to a vertebral body V, which is depicted in dashed lines. The vertebral implant 10 and vertebral body V are shown relative to a coronal plane CP and a sagittal plane SP that are discussed in greater detail below. For now, it should suffice to say that the coronal plane CP and sagittal plane SP are substantially perpendicular to one another and bisect the vertebral implant 10 as shown. The vertebral implant 10 is positioned substantially within the cortical rim R of the vertebral body V. Further, the vertebral implant 10 is positioned in contact with one of the end plates P of the vertebral body V. Accordingly, the vertebral implant 10 includes a superior surface 14 and an inferior surface 16 that approximately match the natural morphology of vertebral bodies V in the human spine.

Figure 3:
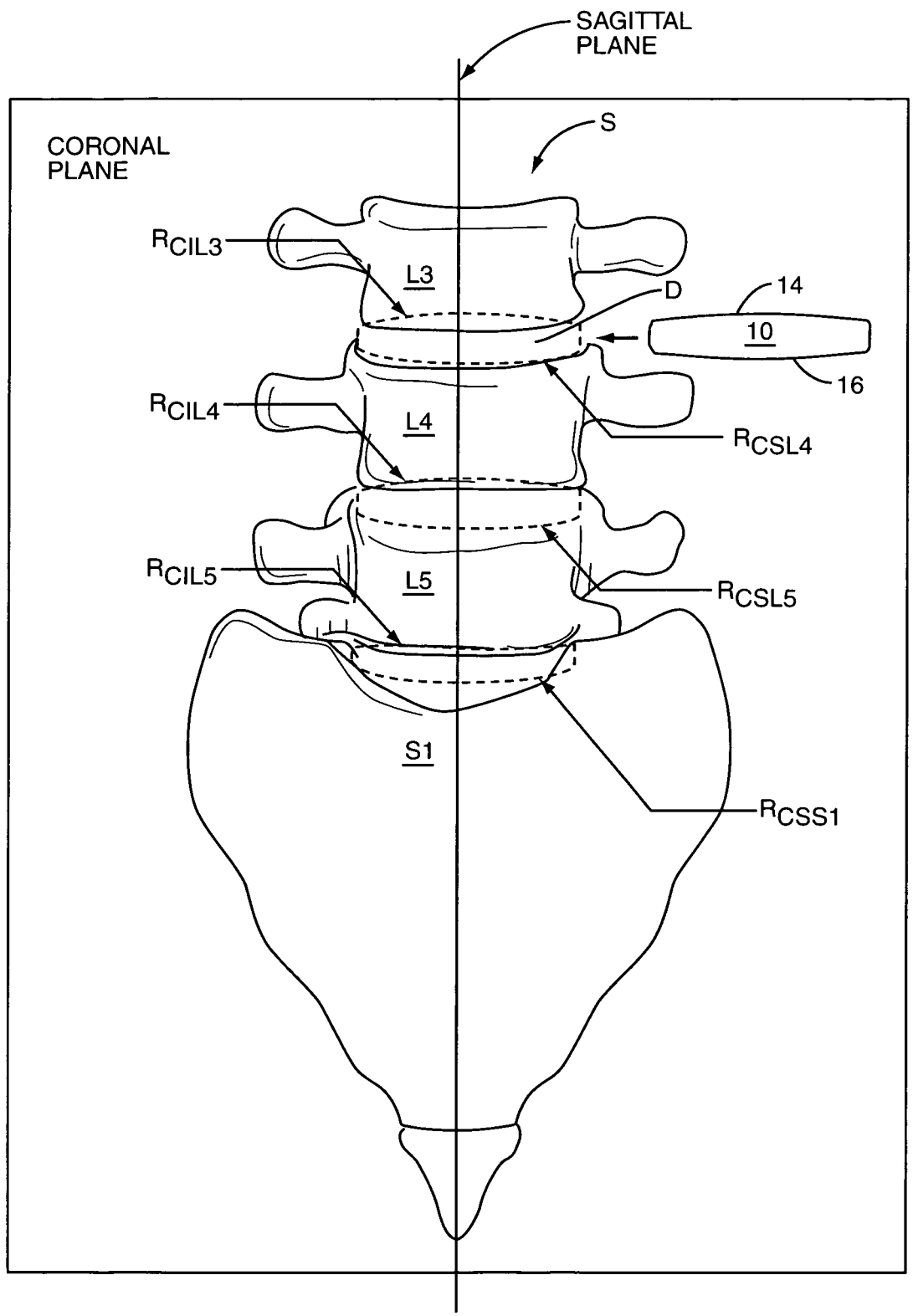
FIG. 3 is an anterior view of a portion of a human spine indicating vertebral morphology in a direction parallel to the coronal plane.
Figure 4:
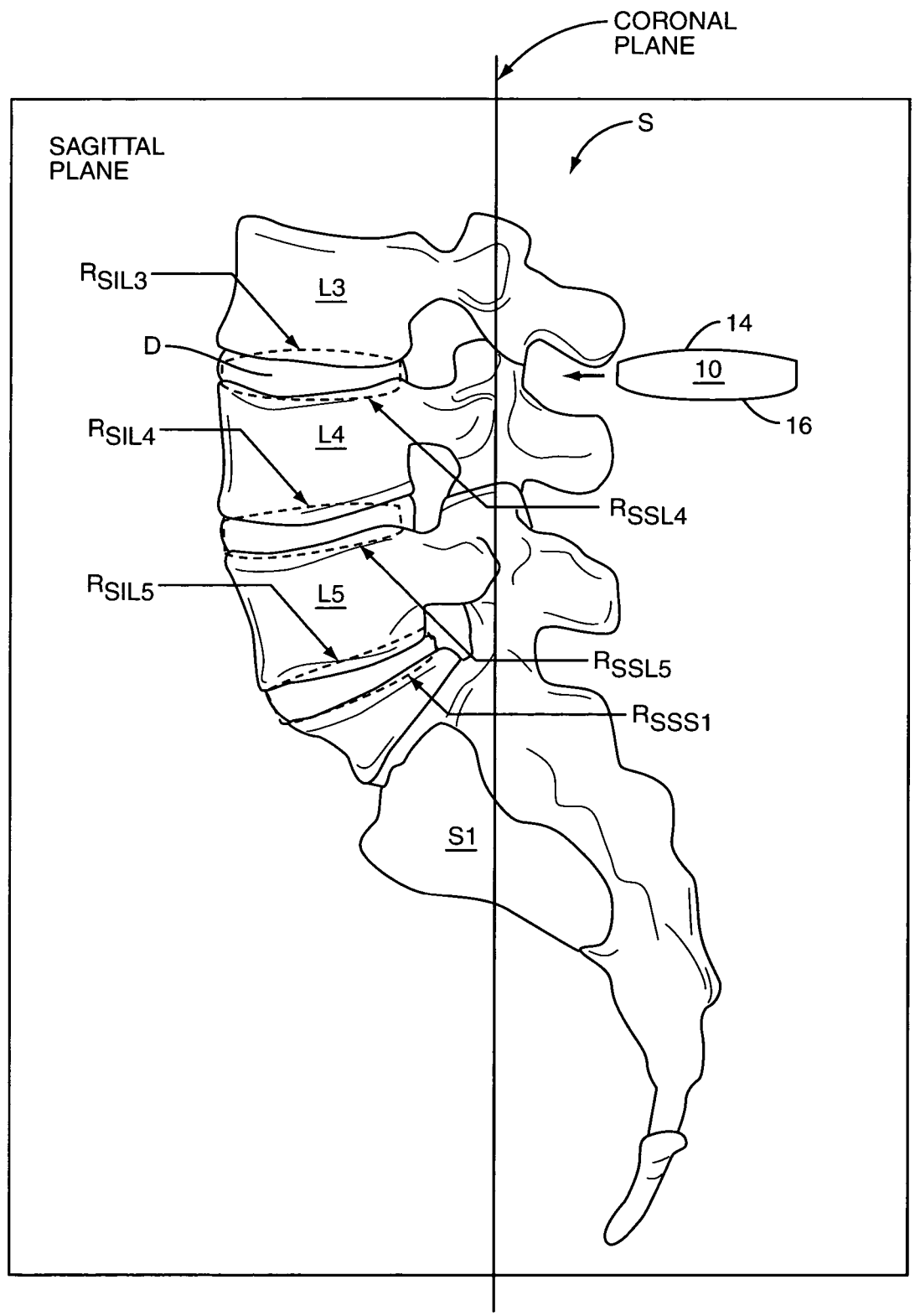
FIG. 4 is a lateral view of a portion of a human spine indicating vertebral morphology in a direction parallel to the sagittal plane.

FIGS. 3 and 4 illustrate this anatomy for a representative portion of a human spine S, which is depicted in dashed lines. Specifically, FIGS. 3 and 4 depict views of a lower lumbar portion of a spine S shown below the L3 level. Further, FIG. 3 is shown from a direction substantially normal to the coronal plane, which is the imaginary plane that separates the body into the anterior and posterior halves. By comparison, FIG. 4 is shown from a direction substantially normal to the sagittal plane, which is the imaginary plane that bilaterally separates the body into left and right halves.

Each FIGS. (3 and 4) also identifies six discrete radius dimensions R related to vertebral bodies L3-L5, S1 in the example shown. Each radius callout includes four subscripts that identify: (1) the plane within which the radius is measured, (2) whether the radius relates to an inferior or superior surface of a vertebral body, and (3) the vertebral body to which the radius relates. For example, the uppermost radius callout in FIG. 3 identifies radius $R_{CIL3}$. With this naming convention, the "C" refers to the coronal plane, the "I" refers to the inferior surface, and "L3" refers to vertebral body L3. By comparison, the lowermost radius callout in FIG. 4 identifies radius $R_{SSS1}$. With this naming convention, the first "S" refers to the sagittal plane, the second "S" refers to the superior surface, and "S1" refers to the sacrum S1. A similar convention is used for the remaining radius callouts.

Figure 5:
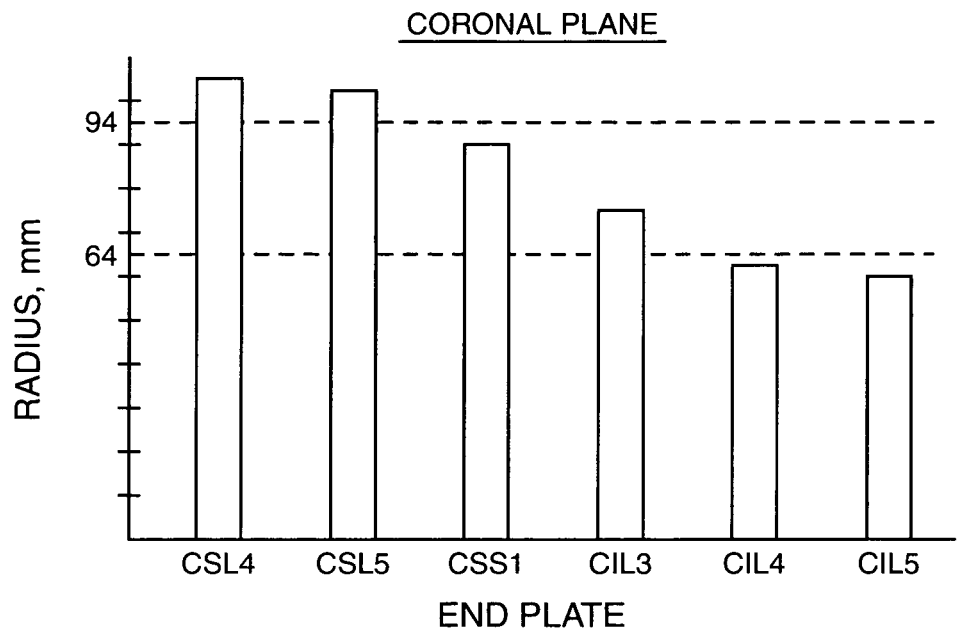
FIG. 5 is bar graph indicating representative curvatures for exemplary vertebral endplates measured in a direction parallel to the coronal plane.
Figure 6:
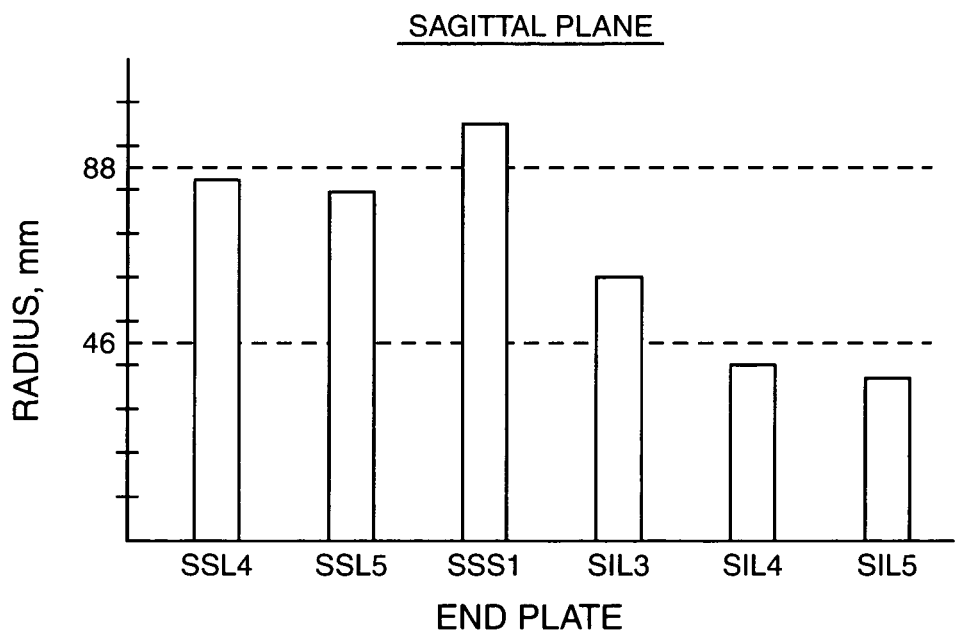
FIG. 6 is bar graph indicating representative curvatures for exemplary vertebral endplates measured in a direction parallel to the coronal plane.

A radiographic analysis of three-dimensional computed tomography (3D-CT) reconstructions of human subjects was performed to identify a morphological relationship between pairs of vertebral bodies. The results of radius measurements taken according to the radii in FIGS. 3 and 4 are shown in FIGS. 5 and 6, respectively. Specifically, FIGS. 5 and 6 illustrate numerical averages for the specific radii taken from multiple human subjects. In each bar graph, the vertical axis represents a radius of curvature taken in the respective planes (coronal for FIG. 5 and sagittal for FIG. 6). The horizontal axis represents a specific end plate of a vertebral body. Generally, the superior surfaces are on the left side of each graph while the inferior surfaces are on the right side on each graph. Each graph also includes two dashed horizontal lines representing an average radius. The upper average radius is associated with the superior vertebral surfaces. The lower average radius is associated with the inferior vertebral surfaces. Notably, the inferior vertebral surfaces are generally characterized by smaller radii than the superior vertebral surfaces.

When plotted as shown in FIGS. 5 and 6, the values suggest a relationship between the curvature of opposed vertebral endplates. This relationship may be used in constructing the superior 14 and inferior 16 surfaces of a vertebral implant 10. For example, a disc D in FIG. 3 may be replaced by the exemplary vertebral implant 10. Accordingly, the superior surface 14 and inferior surface 16 of the vertebral implant 10 are configured to approximately match the natural morphology of the L3 and L4 bodies. More specifically, the superior surface 14 of the vertebral implant 10 is configured to include a curvature that approximately matches the inferior curvature of the L3 vertebra $R_{CIL3}$, $R_{SIL3}$. Similarly, the inferior surface 16 of the vertebral implant 10 is configured to include a curvature that approximately matches the superior curvature of the L4 vertebra $R_{CSL4}$, $R_{SSL4}$. Furthermore, the vertebral implant 10 is configured to include curvatures that approximately match the inferior curvature of the L3 vertebra and superior curvature of the L4 vertebra in both the sagittal and coronal planes. That is, the superior surface 14 and inferior surface 16 of the exemplary implant 10 may also include different radii of curvature in different directions. In one embodiment, the superior surface 14 and inferior surface 16 of the vertebral implant comprise spherical radii that most closely match the overall curvature of the vertebral bodies.

Figure 7:
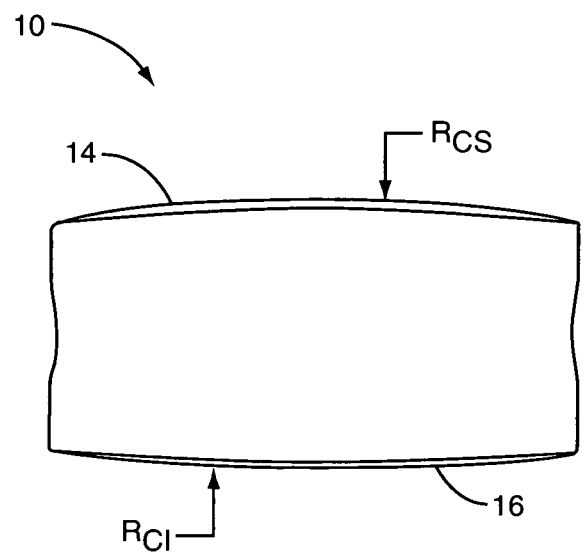
FIG. 7 is an anterior view of a vertebral implant according to one or more embodiments.
Figure 8:
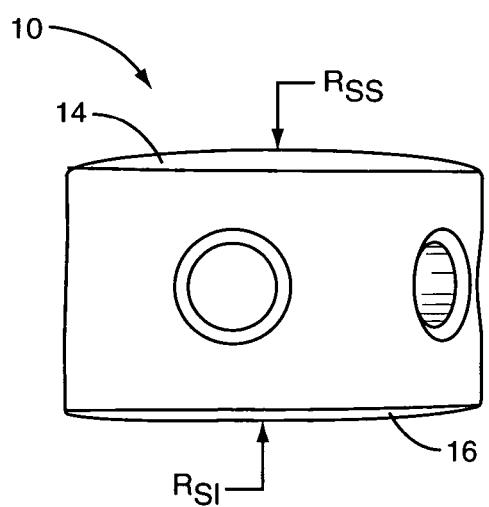
FIG. 8 is a lateral view of a vertebral implant according to one or more embodiments.

In view of these curvature constraints, the relationship between the curvature of the superior surface 14 and inferior surface 16 may be determined through analysis of the data presented in FIGS. 5 and 6. The curvature of the superior surface 14 and inferior surface 16 of the vertebral implant 10 are indicated in FIGS. 7 and 8. FIG. 7 shows a view of the vertebral implant 10 taken from the direction indicated by the view lines in FIG. 2. This direction is substantially normal to the coronal plane. FIG. 8 also shows a view of the vertebral implant 10 taken from the direction indicated by the view lines in FIG. 2, which is from a direction substantially normal to the sagittal plane.

The radii $R_{CS}$, $R_{CI}$ shown in FIG. 7 correspond to radii of curvature as measured within the coronal plane (or a plane parallel to the coronal plane). The subscript designators in FIG. 7 follow a similar convention to those radii identified in FIGS. 3 and 4. For instance, the first letter "C" identifies that the radius is measured within the coronal plane, the second letter "S" or "I" identifies the superior or inferior surface of the implant 10. In one embodiment, the radii $R_{CS}$, $R_{CI}$ approximately match the $R_{CIL3}$, and $R_{CSL4}$ radii from FIG. 3. That is, the radii $R_{CS}$, $R_{CI}$ are approximately 72-75 mm and 98-100 mm, respectively. Thus, the superior surface 14 is constructed with a smaller radius of curvature than the inferior surface 16. This radius may be confined to a direction parallel to the coronal plane or may be a spherical radius.

Similarly, FIG. 8 shows that radii $R_{SS}$, $R_{SI}$ of curvature as measured within the sagittal plane. According to the representative numbers shown in FIG. 4, the radii $R_{SS}$, $R_{SI}$ for the superior 14 and inferior 16 surfaces of the vertebral implant 10 may be approximately 52-55 mm and 85-88 mm, respectively. Once again, the superior surface 14 is constructed with a smaller radius of curvature than the inferior surface 16. As above, this radius may be confined to a direction parallel to the sagittal plane or may be a spherical radius.

From these and the remaining numbers shown in FIGS. 5 and 6, it is apparent that the morphology of vertebral bodies L3 and L4 reflect different curvatures in the coronal and sagittal directions. The vertebral implant 10 may be constructed with a spherical radius that most closely approximates the overall curvature of the vertebral bodies. Simple averaging of the radii in the coronal and sagittal planes reveals that the curvature of the superior surface 14 is on the order of about 65-70% of the curvature of the inferior surface 16. Furthermore, while these numbers have been approximated based on a single disc D location (as shown in FIGS. 3 and 4), the data presented in FIGS. 5 and 6 reveal that a similar relationship generally holds true for each of the locations.

Specifically, the ratio of the curvature of the superior surface 14 and the inferior surface 16 of the vertebral implant 10 based upon the numbers for the coronal plane range between about 60% and 74%. Similarly, the ratio of the curvature of the superior surface 14 and the inferior surface 16 of the vertebral implant 10 based upon the numbers for the sagittal plane range between about 41% and 63%. The vertebral implant 10 may be constructed with a radius in the coronal and sagittal planes at the superior surface 14 and inferior surface 16 that minimizes curvature mismatch between the vertebral implant 10 and the mating vertebral bodies. In one embodiment, the superior surface 14 may be constructed with a radius of curvature in the coronal and sagittal planes that is on the order of about 50-70% of a radius of the inferior surface 16.

In one embodiment, vertebral implant 10 may be constructed with a spherical radius at the superior surface 14 and inferior surface 16 that minimizes curvature mismatch between the vertebral implant 10 and the mating vertebral bodies. In one embodiment, the superior surface 14 may be constructed with a spherical radius that is on the order of about 50-70% of a spherical radius of the inferior surface 16. In one embodiment, the superior surface 10 may be constructed with a spherical radius that is on the order of about 58-62% of a spherical radius of the inferior surface 16. In one embodiment, the radius of curvature of the superior surface 14 of the vertebral implant 10 is between about 55-75 mm. In one embodiment, the radius of curvature of the superior surface 14 of the vertebral implant 10 is between about 40-55 mm. In one embodiment, the radius of curvature of the inferior surface 16 of the vertebral implant 10 is between about 80-100 mm.

In certain implementations, a curvature match in one plane may be more important than another. For instance, other spinal implants such as rods, plates, or spacers may be used to inhibit motion in one direction or another. Therefore, the superior surface 14 may be constructed with a spherical radius that more closely matches the radius of the mating vertebral bodies measured about the coronal plane only. Thus, in one embodiment, the superior surface 14 of the vertebral implant 10 is constructed with a spherical radius between about 55-75 mm (or about 60%-74% of a spherical radius of the inferior surface 16). Similarly, the superior surface 14 may be constructed with a spherical radius that more closely matches the radius of the mating vertebral bodies measured about the sagittal plane only. Thus, in one embodiment, the superior surface 14 of the vertebral implant 10 is constructed with a spherical radius between about 40-55 mm (or about 41%-63% of a spherical radius of the inferior surface 16).

The data in FIGS. 5 and 6 further illustrates that the difference in the radius of curvature in the different directions for the superior surfaces of the vertebrae does not vary as greatly as compared to the inferior surfaces. Note that the average curvature in the coronal plane for the superior surfaces of the vertebrae is about 94 mm while the average curvature in the sagittal plane for the superior surfaces of the vertebrae is about 88 mm. The difference between these average values is only about 6 mm. Contrast this with a difference of about 18 mm (64 mm-46 mm) for the inferior vertebral surfaces. Accordingly, the inferior surface 16 of the vertebral implant 10 may be constructed with a spherical radius that is between about 80 and 100 mm. In one embodiment, the inferior surface 16 of the vertebral implant 10 may be constructed with a spherical radius that is between about 88 and 94 mm. In one embodiment, the vertebral implant 10 may include a uniform, spherical radius for the inferior surface 16 and different radii of curvature in the coronal and sagittal planes for the superior surface 14.

Figure 9:
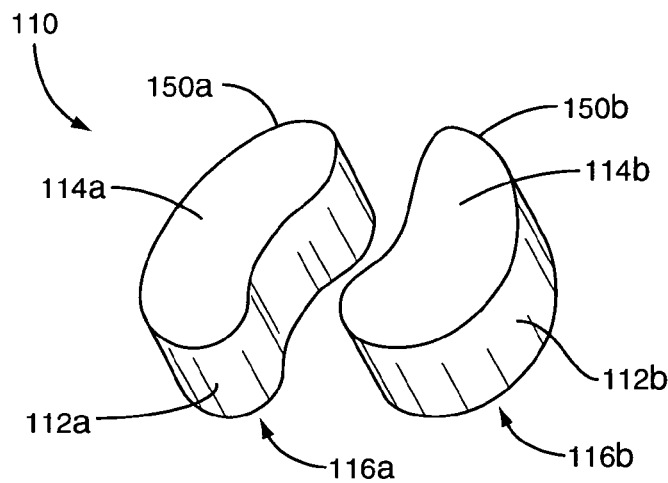
FIG. 9 is a perspective view of a vertebral implant according to one or more embodiments.
Figure 10:
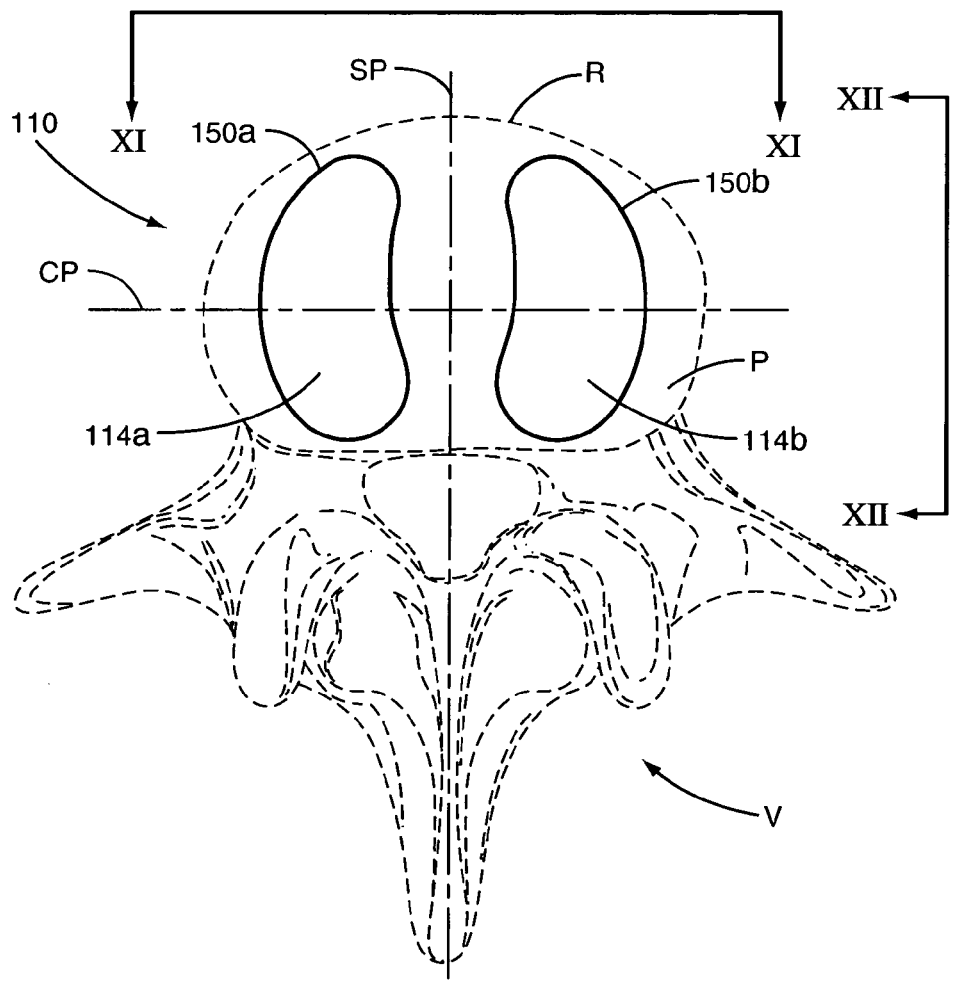
FIG. 10 is a top view of a vertebral implant according to one or more embodiments shown relative to a vertebral body.
Figure 11:
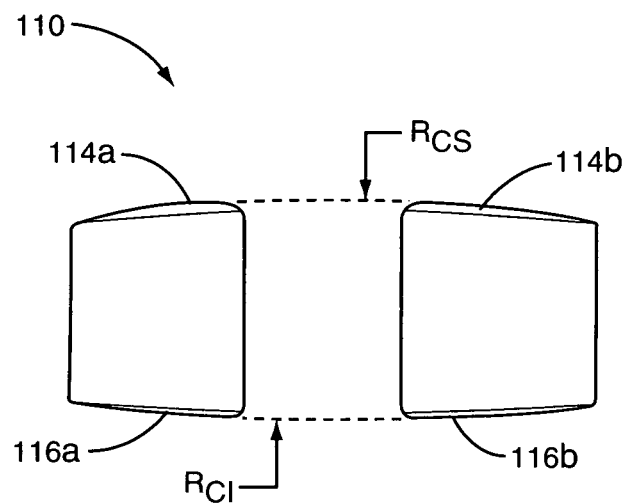
FIG. 11 is an anterior view of a vertebral implant according to one or more embodiments.

Embodiments described above have pertained to a vertebral implant 10 that is constructed of a single body. However, the curvature of the bone contact surfaces may be extended to implants comprising multiple contact surfaces. For example, FIGS. 9-12 illustrate an embodiment of a vertebral implant 110 comprising two halves 150a, 150b. These halves 150a, 150b may represent mirror images of one another, though this is not expressly required. The exemplary vertebral implant 110 is implanted with the halves 150a, 150b positioned on opposite sides of a sagittal plane SP as shown in FIG. 10. The relatively small size of the vertebral implant 110 lends itself to either a posterior or anterior installation. Each half 150a, 150b includes a superior surface 114a, 114b, respectively, that is positioned in contact with an inferior vertebral surface (not shown, but see FIGS. 3 and 4). Further, each half 150a, 150b includes an inferior surface 116a, 116b, respectively, that is positioned in contact with a superior vertebral surface (also not shown, but see FIGS. 3 and 4). FIG. 9 shows a perspective view of the implant 110, while FIG. 10 shows a top view shown oriented relative to a vertebral body V, which is depicted in dashed lines FIG. 11 shows an anterior view of the vertebral implant 110 according to the view lines shown in FIG. 10. FIG. 11 also shows that the superior surfaces 114a, 114b follow a similar curvature identified by radius callout $R_{CS}$. As above, this callout identifies a radius of curvature in the coronal plane. Similarly, the inferior surfaces 116a, 116b follow a similar curvature identified by radius callout $R_{CI}$, which represents a radius of curvature in the coronal plane.

Figure 12:
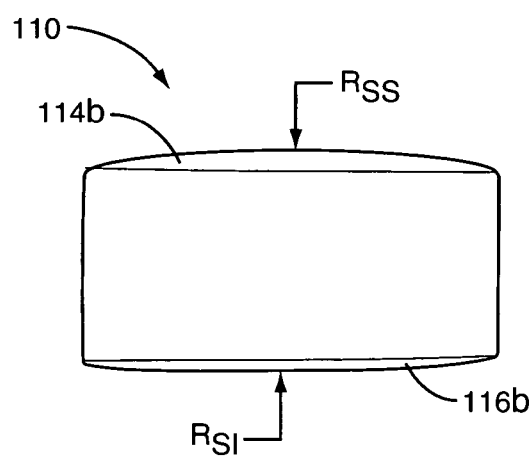
FIG. 12 is a lateral view of a vertebral implant according to one or more embodiments.

FIG. 12 shows a lateral view of the vertebral implant 110 according to the view lines shown in FIG. 10. FIG. 12 also shows that the superior surfaces 114a, 114b follow a similar curvature identified by radius callout $R_{SS}$, which represents a radius of curvature in the sagittal plane. Similarly, the inferior surfaces 116a, 116b follow a similar curvature identified by radius callout $R_{SI}$, which identifies a radius of curvature in the sagittal plane.

As with the above described embodiments, the superior surfaces 114a, 114b and inferior surfaces 116a, 116b may be defined by curvatures that are different in the coronal and sagittal directions. Alternatively, the superior surfaces 114a, 114b and inferior surfaces 116a, 116b may be defined by curvatures that are the same in the coronal and sagittal directions. In one embodiment, the superior surfaces 114a, 114b and inferior surfaces 116a, 116b are defined by spherical radii. The relationship between the relative curvatures of the superior surfaces 114a, 114b and inferior surfaces 116a, 116b may be defined by the percentages and size ranges discussed above.

Embodiments described above have pertained to vertebral implants 10, 110 in which superior and inferior bone contact surfaces are located on the same body. However, this is not expressly required. The curvature of the respective bone contact surfaces may be disposed in separate implants or separate implant members such as the vertebral implant 210 shown in FIGS. 13 and 14. The vertebral implant 210 represents a spinal arthroplasty device and comprises three main components: a first end plate 212, a second end plate 214, and a nucleus 216. FIG. 14 provides an exploded, cross-section view of the components taken along the section line from FIG. 13. In the orientation shown, the first end plate 212 is a superior end plate while the second end plate 214 is an inferior end plate.

Each end plate 212, 214 may include a respective bone interface surface 218, 220 that is placed in contact with a corresponding a vertebral member (not shown). The nucleus 216 is positioned between the end plates 212, 214. The interface between the nucleus 216 and the first end plate 212 is a sliding interface that allows for sliding motion of the nucleus 216 relative to the first end plate 212. The arrow labeled A in FIG. 14 illustrates this sliding motion. This arrow A suggests motion in a direction parallel to the page. However, the mating surfaces 226, 228 at the interface between the nucleus 216 and first end plate 212 is substantially spherical. Consequently, the sliding motion at the interface between the nucleus 216 and the first end plate 212 may occur in virtually all directions relative to a central axis X. In an alternative embodiment, the mating surfaces 226, 228 may be cylindrical, thus limiting sliding motion to the direction of the arrow labeled A.

A similar interface exists between the nucleus 216 and the second end plate 214. In the example shown, the second nucleus bearing surface 230 and second end plate bearing surface 232 are also spherical surfaces. Consequently, the sliding motion at the interface between these components 216, 214 (identified by arrow B) may occur in virtually all directions relative to a central axis X. Motion of the nucleus 216 relative to the second end plate 214 is constrained by the annular recess 234 that is disposed between the second end plate bearing surface 232 and an outer annular rim 236. The outer annular rim 236 inhibits further sliding motion between the nucleus 216 and the second end plate 214. Thus, the nucleus 216 may remain in a sandwiched configuration between the first and second end plates 212, 214.

Figure 13:
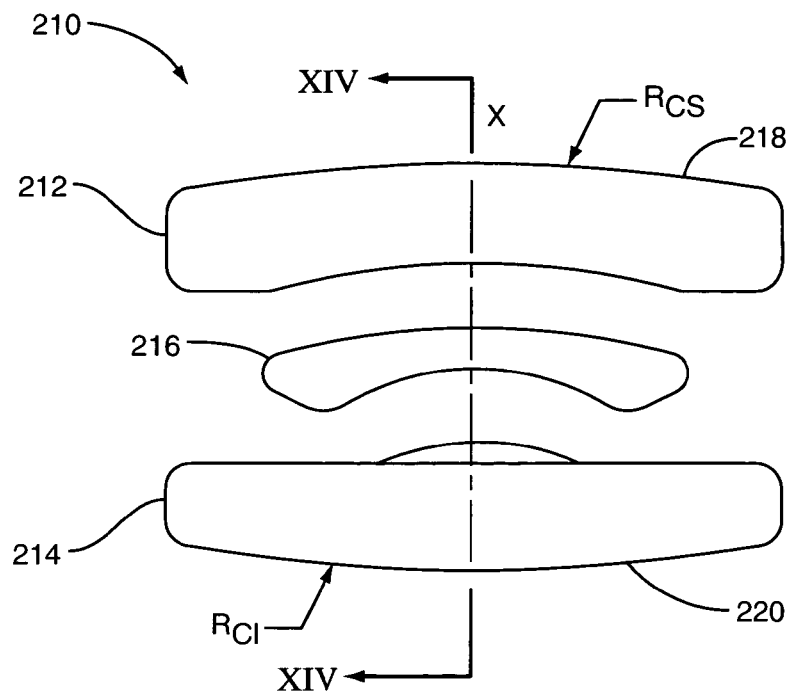
FIG. 13 is an anterior view of a vertebral implant according to one or more embodiments.
Figure 14:
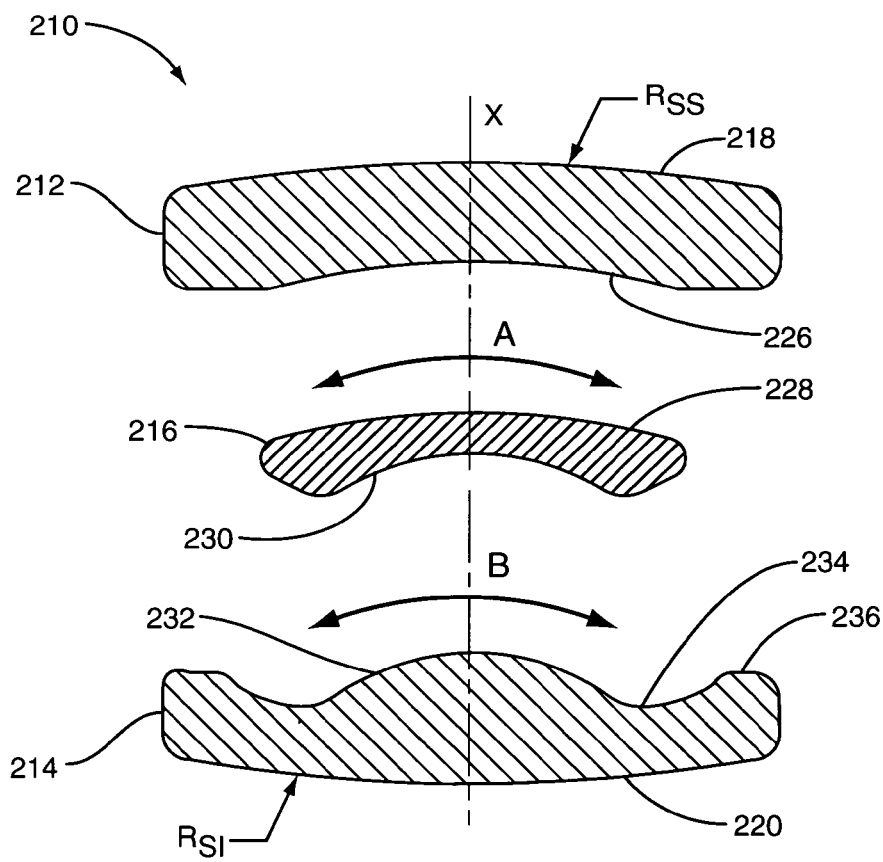
FIG. 14 is a lateral view of a vertebral implant according to one or more embodiments.

FIG. 13 shows that the superior surface 218 of the first end plate 212 is defined by a curvature $R_{CS}$. As described above, this callout identifies a radius of curvature in the coronal plane at the superior surface 218 of the first end plate 212. Similarly, the inferior surface 220 is defined by a curvature $R_{CI}$, which identifies a radius of curvature in the coronal plane at the inferior surface 220 of the second endplate 220. By comparison, FIG. 14 shows that the superior surface 218 is defined by radius $R_{SS}$, which identifies a radius of curvature in the sagittal plane at the superior surface 218 of the first end plate 212. Similarly, the inferior surface 220 is defined by a curvature $R_{SI}$, which identifies a radius of curvature in the sagittal plane at the inferior surface 220 of the second endplate 214.

As with the above-described embodiments, the superior surface 218 and inferior surface 220 may be defined by curvatures that are different in the coronal and sagittal directions. Alternatively, the superior surface 218 and inferior surface 220 may be defined by curvatures that are the same in the coronal and sagittal directions. In one embodiment, spherical radii define the superior surface 218 and inferior surface 220. The relationship between the relative curvatures of the superior surface 218 and inferior surface 220 may be defined by the percentages and size ranges discussed above.

The vertebral implant 210 shown in FIGS. 13 and 14 is configured to restore motion between vertebral bodies. In other procedures, such as vertebrectomies or corpectomies, one or more vertebral bodies are removed and an implant is inserted in the space left by the removed vertebrae. These types of devices (not shown) include multiple components similar to the implant 210 shown in FIGS. 13 and 14. However, in lieu of a nucleus 216, these types of devices may include spacers, a cage, rods, or other fixed or expandable members spanning a distance between first and second end plates. The various contours for the bone-contact surfaces described above may be used with these types of devices as well as those disclosed herein.

Furthermore, embodiments disclosed above have not included any particular surface geometry, coating, or porosity as are found in conventionally known vertebral implants. Surface features such as these are used to promote bone growth and adhesion at the interface between an implant and a vertebral end plate. Examples of features used for this purpose include, for example, teeth, scales, keels, knurls, and roughened surfaces. Some of these features may be applied through post-processing techniques such as blasting, chemical etching, and coating, such as with hydroxyapatite. The bone interface surfaces may also include growth-promoting additives such as bone morphogenetic proteins. Alternatively, pores, cavities, or other recesses into which bone may grow may be incorporated via a molding process. Other types of coatings or surface preparation may be used to improve bone growth into or through the bone-contact surfaces. However, the overall curvature of surfaces that include these types of features may still be defined by the dimensional relationships disclosed herein.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. For instance, the measured morphological features disclosed above are presented in FIGS. 3-6 for a representative region of the spine. The same types of values may be applicable for other regions of the spine, including for example, the upper lumbar, thoracic, and cervical regions of the spine. The present embodiments are, therefore, to be considered in all respects as illustrative and not restrictive, and all changes coming within the meaning and equivalency range of the appended claims are intended to be embraced therein.

What is claimed is:

1. A vertebral implant for insertion into an intervertebral space between first and second vertebral bodies within a patient comprising:
 a superior surface disposed at a first side of the implant to contact the first vertebral body; and
 an inferior surface disposed at a second, opposite side of the implant to contact the second vertebral body;
 the inferior surface including a first radius of curvature within a first plane that extends through the superior and inferior surfaces and bisects the implant;
 the superior surface including a second radius of curvature within the first plane, the second radius being between about 60 percent to about 74 percent of the first radius.

2. The implant of claim 1 wherein the first plane is a coronal plane.

3. The implant of claim 1 wherein the first and second radius define a spherical radius.

4. The implant of claim 1 wherein the superior surface includes a third radius of curvature within a second plane that is substantially perpendicular to the first plane.

5. The implant of claim 4 wherein the third radius of curvature is between about 41 percent to about 63 percent of the first radius.

6. The implant of claim 4 wherein the second plane is a sagittal plane.

7. The implant of claim 1 wherein the implant is a lower lumbar implant.

8. The implant of claim 1 wherein the superior surface and the inferior surface are disposed on a single implant body.

9. The implant of claim 1 wherein the superior surface and the inferior surface are disposed on different end plates.

10. A vertebral implant for insertion into an intervertebral space between first and second vertebral bodies within a patient comprising:
 a superior surface disposed at a first side of the implant to contact the first vertebral body, the superior surface defined by a first spherical radius;
 an inferior surface disposed at a second, opposite side of the implant to contact the second vertebral body, the inferior surface defined by a second spherical radius;
 the first spherical radius being between about 60 to about 74 percent of the second spherical radius.

11. The implant of claim 10 wherein the first spherical radius is between about 55 mm and about 75 mm.

12. The implant of claim 10 wherein the second spherical radius is between about 80 mm and about 100 mm.

13. The implant of claim 10 wherein the implant is a lower lumbar implant.

14. The implant of claim 10 wherein the superior surface and the inferior surface are disposed on a single implant body.

15. The implant of claim 10 wherein the superior surface and the inferior surface are disposed on different end plates.

16. A vertebral implant for insertion into an intervertebral space between first and second vertebral bodies within a patient comprising:
 a superior surface disposed at a first side of the implant to contact the first vertebral body; and
 an inferior surface disposed at a second, opposite side of the implant to contact the second vertebral body;
 the inferior surface including a first radius of curvature within a first plane that extends through the superior and inferior surfaces and bisects the implant, the first radius being within a range between about 80 mm and about 100 mm;
 the superior surface including a second radius of curvature within the first plane, the second radius being within a range between about 50 mm and about 70 mm.

17. The implant of claim 16 wherein the first plane is a coronal plane.

18. The implant of claim 16 wherein the first plane is a sagittal plane.

19. The implant of claim 16 wherein the first and second radius define a spherical radius.

20. The implant of claim 16 wherein the superior surface includes a third radius of curvature within a second plane that is substantially perpendicular to the first plane.

21. The implant of claim 20 wherein the third radius of curvature is between about 40 mm and about 55 mm.

22. The implant of claim 16 wherein the implant is a lower lumbar implant.

23. The implant of claim 16 wherein the superior surface and the inferior surface are disposed on a single implant body.

24. The implant of claim 16 wherein the superior surface and the inferior surface are disposed on different end plates.

* * * * *